United States Patent [19]

Ooms et al.

[11] Patent Number: 5,141,843
[45] Date of Patent: Aug. 25, 1992

[54] DEVELOPER LIQUID FOR HIGH CONTRAST DEVELOPMENT

[75] Inventors: Richard A. Ooms, Hofstade; Piet Kok, Gent; Jean-Marie O. Dewanckele, Drongen, all of Belgium

[73] Assignee: AGFA-Gevaert N. V., Mortsel, Belgium

[21] Appl. No.: 675,518

[22] Filed: Mar. 27, 1991

[30] Foreign Application Priority Data

Apr. 4, 1990 [EP] European Pat. Off. ........ 90200800.2

[51] Int. Cl.⁵ .............................................. G03C 5/26
[52] U.S. Cl. ................................... 430/489; 430/268; 430/438; 430/448; 430/464; 430/482; 430/566; 548/251
[58] Field of Search ............... 430/268, 438, 448, 464, 430/482, 489, 566, 607, 613; 548/251

[56] References Cited

U.S. PATENT DOCUMENTS 3,645,738  2/1972  Willems et al. ..................... 430/613
4,756,990  7/1988  Ooms et al. ........................ 430/487
4,888,273  12/1989  Himmelwright et al. ........... 430/611

Primary Examiner—Hoa Van Le

[57] ABSTRACT

A developer liquid suited for use in development of photographic silver halide emulsion layer materials which liquid contains:

1) hydroquinone or a substituted hydroquinone as sole developing agent or said hydroquinone as main developing agent in combination with an auxiliary developing agent in an amount less than 10 mole % with respect to the main developing agent,
2) an inorganic compound yielding free sulphite ions in an amount of at least 5 grams per liter,
3) an organic anti-fogging agent corresponding to the following general formula (Z):

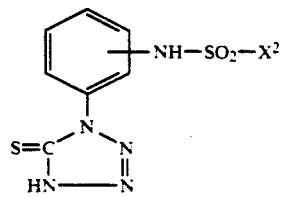

wherein:

$X^2$ represents an alkyl group or an aryl group including said groups in substituted form or an amino group including said group in substituted form;
the amount of anti-fogging agent being in the range of 50 mg to 1 g per liter,
4) a polymer containing a plurality of alkylene oxide units, and
5) the necessary alkaline material to have in said liquid a pH of at least 10.5. Optional additives can also be present in the developing liquid.

19 Claims, No Drawings

DEVELOPER LIQUID FOR HIGH CONTRAST DEVELOPMENT

1. FIELD OF THE INVENTION

This invention relates to a method of effecting high contrast development of an image-wise exposed photographic silver halide emulsion layer material and to a development liquid used therefor.

2. BACKGROUND OF THE INVENTION

In the reproduction of continuous tone information for mechanical printing purposes, it is customary to make a half-tone photographic intermediate, usually a film negative, in which the gradations in tone are represented by dots of differing size. The quality of the resulting halftone picture is closely connected with the shape, spectral density, and uniformity of the dots of the half-tone print.

In order to obtain very high-contrast screen dots in halftone images it has been practice to formulate developers, so-called lith-developers, containing essentially a p-dihydroxybenzene such as hydroquinone, an alkali, an alkali metal bromide and a low level of free sulphite ions.

Very high contrast results, preferably with gamma above 10, also called "lith-gradation", can be obtained with said high-contrast developers and so-called "lith silver halide emulsion materials". In these materials the silver halide comprises at least 50 mole % of chloride, the balance, if any, being bromide and optionally a minor amount of iodide.

Hydroquinone developers having a low sulphite ion concentration are commonly referred to as "lith-type developers" and their mechanism of operation is described by J. A. C. Yule in the Journal of the Franklin Institute, 239 (1945), pages 221 to 230.

In conventional "lith" developers the low sulfite ion concentration is inadequate to provide effective protection against aerial oxidation. As a result, a conventional "lith" developer is lacking in stability and tends to give erratic results depending on the length of time that it has been exposed to air.

As explained e.g. in U.S. Pat. No. 4,081,280 it is necessary when using a lith-developer with low free sulphite content to replenish carefully the developer solution compensating:

(1) for developer exhaustion by aerial oxidation, and
(2) for use of developer in function of the treated exposed photographic material.

According to U.S. Pat. No. 3,972,719 in order to be less dependent on replenishment for aerial oxidation a high contrast developer with relatively high sulphite content and an anti-fogging nitro-compound is provided. Said developer contains not more than 0.05 g/liter of any auxiliary developing agent that shows a superadditive developing effect with a p-dihydroxybenzene developing agent and may contain a polymer containing a plurality of alkylene oxide units, i.e. a polymeric oxyalkylene compound, for controlling the development speed.

According to published European Patent Application 0 196 705 a method of effecting high contrast development of an imagewise exposed photographic silver halide emulsion layer material is carried out in an aqueous medium having a pH of 10 to 12 containing:

a)
(i) hydroquinone or a substituted hydroquinone,
(ii) an auxiliary developing agent having a developing activity of such degree as to give when utilized in the Standard Development Test defined in the specification a relative development rate $f_x$ in the range of about 1-2, b) free sulphite ions in an amount of at least 5 g per liter, and c) an organic anti-fogging agent corresponding to one of the following general formulae (A) and (B):

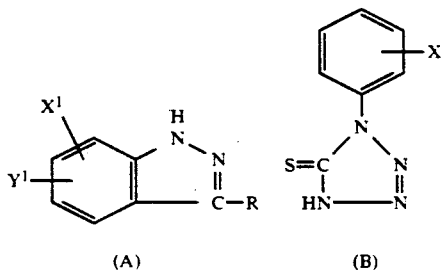

(A)            (B)

wherein:

$Y^1$ is a nitro-substituent in the 5- or 6-position of the indazole nucleus,
$X^1$ is hydrogen or a sulphonic acid group in salt form,
R is hydrogen or a lower ($C_1$-$C_5$) alkyl group,
X is a substituent being or containing a carboxyl group or sulphonic acid group in salt form, d) a polymer containing a plurality of alkylene oxide units and having a molecular weight of at least 1500, and said ingredients a) to d) being present in the aqueous developing medium in such relative amounts that development therein of the exposed photographic material carrying a latent continuous tone wedge image under the same development conditions given the density versus log exposure sensitometric curve of the resulting silver wedge would have a) a maximum gradient ($\gamma$) of at least 5.0 between the log exposure values measured at densities of 0.3 and 3.0 above fog on the log exposure scale and b) a gradient ($\gamma_v$) of at least 2.0 in the toe between the log exposure values measured at densities of 0.1 and 0.6 above fog on the log exposure scale.

Until recently the characteristic of lith-development resulting in a particularly high gradation necessary for sharp screen dot reproduction was restricted to the use of silver halide emulsion layers the silver halide of which was mainly silver chloride.

According to U.S. Pat. No. 4,710,451 a method of effecting high contrast development of an image-wise exposed photographic silver halide emulsion layer material is provided, wherein an image-wise exposed silver halide emulsion material the silver halide of which is at least 90 mole percent silver bromide, the remainder if any, being chloride and/or iodide is developed in a developing medium containing hydroquinone as sole developing agent, a large amount of sulphite (at least 5 g per liter of free sulphite ions), a nitro-indazole as anti-fogging agent, a polyoxyethylene polymer having a molecular weight of at least 1500 and an inorganic alkaline compound to impart to the developing medium a pH of at least 10.5.

Since the nitro-indazole and other indazoles such as cyano- and halo-indazoles, particularly 5-cyano and 5-chloro-indazole, are instable in alkaline medium and loose their anti-fogging activity and development retarding activity, the developer formulation is kept in concentrated form in two parts before use an combined and diluted to the desired strength with water, the nitroindazole antifogging agent(s) and polyoxyalkylene polymer being kept before use in acid medium in one part and the other ingredients in alkaline medium in the other part. Although by said procedure the stability problem is solved it would be more convenient if one could utilize only a single liquid high contrast developer that does not suffer from degradation on storage and use and avoid the need for separate media that have to be combined before use.

3. SUMMARY OF THE INVENTION

It is an object of the present invention to provide a method of high contrast development of an imagewise exposed silver halide emulsion layer with a developer liquid containing an anti-fogging agent that has a good stability in alkaline aqueous medium.

It is a further object of the present invention to provide an aqueous alkaline liquid for high gradation development of an imagewise exposed photographic silver halide emulsion material wherein said liquid contains an anti-fogging agent having a good stability against alkali.

Other objects and advantages of the present invention will appear from the further description and examples.

According to the present invention a developer liquid suited for use in the development of photographic silver halide emulsion layer materials contains:

1) hydroquinone or a substituted hydroquinone as sole developing agent or said hydroquinone as main developing agent in combination with an auxiliary developing agent in an amount less than 10 mole % with respect to the main developing agent,
2) an inorganic compound yielding free sulphite ions in an amount of at least 5 grams per liter,
3) an organic anti-fogging agent corresponding to the following general formula (Z):

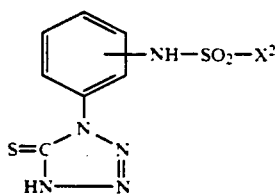

(Z)

wherein:
$X^2$ represents an alkyl group or an aryl group including said groups in substituted form or an amino group including said group in substituted form;
the amount of anti-fogging agent being in the range of 50 mg to 1 g per liter,
4) a polymer containing a plurality of alkylene oxide units, and
5) the necessary alkaline material to have in said liquid a pH of at least 10.5, preferably between 10.8 and 11.8.

Further the present invention provides a method for high contrast development of an image-wise exposed photographic silver halide emulsion layer material, the development being carried out by contacting the photo-exposed photographic material with an aqueous alkaline developer liquid, having a pH of at least 10.5, preferably having a pH in the range of 10.8 to 11.8, in the presence of ingredients 1) to 4) as follows:

1) hydroquinone or a substituted hydroquinone as sole developing agent or said hydroquinone as main developing agent in combination with an auxiliary developing agent in an amount less than 10 mole % with respect to the main developing agent,
2) an inorganic sulfite compound providing free sulfite ions in an amount of at least 5 grams per liter,
3) an organic anti-fogging agent corresponding to the following general formula (Z):

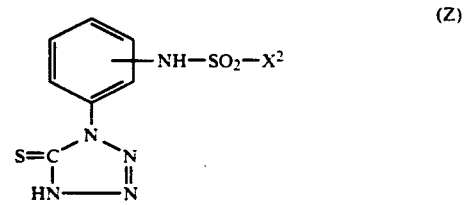

(Z)

wherein:
$X^2$ represents an alkyl group or an aryl group including said groups in substituted form or an amino group including said group in substituted form, and
4) a polymer containing a plurality of alkylene oxide units and having a molecular weight of at least 1500, said ingredients 1), 2), 3) and 4) being present during said development in said aqueous medium in such amounts that when said photographic material is image-wise exposed through a continuous tone wedge and test developed in the thus constituted aqueous developing medium for a time of 45 s at 30° C. and fixed there results a silver wedge image corresponding with a log exposure versus density sensitometric curve wherein the maximum gradient ($\gamma$) is at least 5 and the product of said maximum gradient ($\gamma$) and of the gradient in the toe ($\gamma v$) of said curve is at least 20; the maximum gradient is measured between the log exposure values corresponding with the densities 0.3 and 3.0 above fog of said curve and the gradient in the toe is measured between the log exposure values corresponding with the densities 0.1 and 0.6 above fog of said curve.

4. DETAILED DESCRIPTION OF THE INVENTION

Hydroquinone compounds that are used according to the present invention as main developing agents include unsubstituted hydroquinone and e.g. the following substituted hydroquinones:
chlorohydroquinone,
bromohydroquinone,
isopropylhydroquinone,
toluhydroquinone,
methylhydroquinone,
2,3-dichlorohydroquinone,
2,5-dimethylhydroquinone,
2,3-dibromohydroquinone,
1,4-dihydroxy-2-acetophenone-2,5-dimethylhydroquinone,
2,5-diethylhydroquinone.
2.5-di-p-phenethylhydroquinone,
2,5-dibenzoylaminohydroquinone, or
2,5-diacetaminohydroquinone and mixtures thereof.

The preparation of these hydroquinone compounds is known to those skilled in the art.

Auxiliary developing agents suited for use according to the present invention are e.g. p-amino-phenol, p-methylaminophenol, p-phenylene diamine sulphate, N,N-diethyl-p-phenylene diamine hydrochloride or a 1-phenyl-3-pyrazolidinone type developing agent including the possibility of using a mixture of at least two of them.

Preferred auxiliary developing agents are p-methylaminophenol and 1-phenyl-3-pyrazolidinone type developing agents, e.g. 1-p-carboxyphenyl-4,4-dimethyl-3-pyrazolidinone.

Preference is given likewise to an auxiliary developing agent within the scope of the main claim of U.S. Pat. No. 4,756,990 corresponding with EP 0196705.

The main developing agent and also the auxiliary developing agent may be present in the photographic material, e.g. in a silver halide photographic emulsion layer or in a layer in water-permeable relationship therewith already before development and incorporated therein already in the manufacturing stage. In that case the development may be carried out by contacting the photographic material with an alkaline aqueous liquid free from developing agent(s) but containing ingredient 2) and optionally the other ingredients 3) and/or 4).

The coverage of the developing agent(s) in the photographic material is e.g. in the range of 0.1 to 5 g/m². When applied in the developer liquid the developing agent(s) is (are) preferably used in a concentration in the range of 10 to 60 g/l.

The sulphite ions (ingredient 2) are incorporated into the developer composition starting preferably from an alkaline metal hydrogen bisulphite or metabisulphite or a corresponding ammonium salt. The concentration of free sulphite ion is preferably in the range of 15 to 80 grams per liter.

Preferred representatives of the above defined antifogging compounds according to general formula (Z) are given with their structural formula and melting point (°C.) in the following Table 1.

TABLE 1

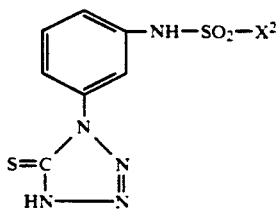

| Compound No. | X² | Melting point °C. |
| --- | --- | --- |
| 1 | —CH₃ | 162.7 |
| 2 | phenyl | 155.4 |
| 3 | p-nitro-phenyl | 157.7 |
| 4 | p-tolyl | 151.5 |
| 5 | p-cetyloxy-phenyl | 125.7 |

The synthesis of said compounds is illustrated by the detailed preparation of compound No. 2 of Table 1.

Preparation of compound No. 2

Preparation of 1-(3-aminophenyl)-5-(4-acetoxybenzylthio)-tetrazole

Intermediate Compound A 2.84 g (0.022 mole) of diisopropylethylamine were added slowly at 20° C. to a stirred suspension of 3.86 g (0.02 mole) of 1-(m-aminophenyl)-5-mercaptotetrazole (prepared as described in GB-P 2,088,849) in 20 ml of acetonitrile. Thereupon 3.6 g (0.02 mole) of p-acetoxybenzylchloride [prepared as described in J. Org. Chem. 43, 1197, (1978)] were added. The resulting reaction mixture was stirred for 3 h at room temperature. Then 50 ml of water were added. The precipitate was filtered with suction, rinsed with water and dried at 50° C.

Yield of compound A: 6.5 g. Melting point: 149.6° C.

Preparation of 1-(3-benzenesulfonamido-phenyl)-5-(4-acetoxybenzylthio)-tetrazole Intermediate Compound B 388.3 g (2.2 mole) of benzenesulfonylchloride was added at 20° C. to a stirred suspension of 682 g (2 mole) of intermediate compound A and 147 g (2.2 mole) of pyridine in 4 liter of acetonitrile. The reaction mixture was stirred for 5 h at room temperature. Thereupon the mixture was poured in 20 liter of water whereto 250 ml of 12N hydrochloric acid were added.

The precipitate was filtered with suction, washed with water and dried.

Yield of compound B: 955 g. Melting point: 132.6° C.

Preparation of 1-[3-(benzenesulfonamido)-phenyl]-5-mercaptotetrazole

Compound No. 2 of Table 1

913.9 g (1.9 mole) of intermediate compound B was added to a solution of 375.5 g (5.7 mole) of potassium hydroxide (85% wt) in 4.75 liter of methanol. The obtained solution was stirred for 3 h at room temperature. 9.5 liter of water were added to the rection mixture and the pH was adjusted to 6. The slightly turbid solution was washed with methylene chloride. The pH of the aqueous supernatant layer was then lowered to zero with 5N hydrochloric acid. The formed precipitate was filtered with suction, rinsed with water and dried.

Yield 573 g; Melting point: 155.5° C.

The anti-fogging agents according to said general formula (Z) may be present in the light-sensitive material already in its manufacturing stage but they are used preferably as one of the ingredients dissolved in the alkaline developer liquid before starting the development.

When present in the photographic material said antifogging agent is applied therein preferably at a coverage up to 100 mg per m².

In the developer liquid the concentration of said antifogging agent is preferably up to 1000 mg per liter.

Suitable polyalkylene oxide polymers also called polymeric oxyalkylene compounds for use according to the present invention are polyalkyleneoxides as such, e.g. polyethylene oxides of a molecular weight above 1500 or condensation products thereof with e.g. alcohols, glycols, phosphoric acids, sulphonic acids, aliphatic amines and diamines. Examples of condensation products containing oxyalkylene units are described e.g. in European Patent 0196705, the United Kingdom Patent Specifications 600,058 filed Jan. 10, 1946 by E. I. du Pont de Nemours, 871,801 filed Nov. 30, 1956 by Kodak, 920,637 filed May 7, 1959, 940,051 filed Nov. 1, 1961, 945,340 filed Oct. 23, 1961, 949,643 filed Nov. 2, 1961, all four by Gevaert Photo-Producten N. V., 991,608 filed Jun. 14, 1961 by Kodak, 1,015,023 filed Dec. 24, 1962, 1,091,705 filed May 20, 1965, both by Gevaert Photo-Producten N. V., 1,107,022 filed Oct. 7, 1965, 1,147,817 filed Aug. 19, 1966, 1,162,135 filed Oct. 11, 1965 and 1,184,434 filed Aug. 30, 1966 all four by Gevaert-Agfa N. V., in the published German Patent Applications 1,141,531 filed Jan. 24, 1962 by Perutz Photowerke G.m.b.H., 1,188,439 filed May 16, 1964 by Fuji Shashin Film Kabushiki Kaisha, and in the U.S. Pat. Nos. 1,970,578 of Conrad Schoeller and Max Wittwer, issued Aug. 21, 1934, 2,240,472 of Donald R. Swan, issued Apr. 29, 1941, 2,423,549 of Ralph K. Blake, William Alexander Stanton, Ferdinand Schulze, issued Jul. 8, 1947, and 2,441,389 of Ralph K. Blake, issued May 11, 1948.

Preferred polyoxyalkylene compounds for use in the present development process are polymers containing an average number of at least 30 repeating oxyethylene units. Particularly good results are obtained with polyoxyethylene compounds having an average number of 70 repeating oxyethylene units. Particularly suited polyoxyethylene polymers for use according to the present invention are disclosed in U.S. Pat. No. 3,947,273 of Pollet et al., issued Mar. 30, 1976. These polymers contain end-groups improving the water-solubility. An example of a preferred polyoxyethylene polymer having ionic end groups corresponds to the following structural formula: $^+X.^-O-SO_2-(CH_2-CH_2-O)_n-CH_2-CH_2-SO_2-O^-.X^+$, wherein n is e.g. 30 to 200, and $X^+$ is a cation, e.g. sodium ion.

The polyoxyalkylene compounds may be present in the photographic material already in its manufacturing stage, e.g. in the silver halide emulsion layer and/or in a layer in waterpermeable relationship therewith at a coverage preferably not surpassing 250 mg per m$^2$. In the developer liquid said compounds are used e.g. in a concentration up to 2500 mg per liter.

Other adjuvants well known to those skilled in the art of developer formulation may be added to the developer liquid used according to the present invention.

A survey of conventional developer addenda is given by Grant Haist in "Modern Photographic Processing" —John Wiley and Sons—New York (1979) p. 220–274. Such addenda are e.g. restrainers, such as the soluble halides, e.g. applied as potassium bromide, organic solvents improving the solubility of developing agents, organic anti-foggants, preservatives, e.g. biocides and buffering agents, e.g. carbonates, phosphates and borates.

The developer liquid used according to the present invention may contain free bromide ions the concentration of which is preferably in the range of 0.5 to 15.0 g per liter of developer solution.

Organic solvent(s) for improving the dissolution of hydroquinone in aqueous medium are described e.g. in U.S. Pat. No. 4,030,920, GB-P 1,343,718 and FR-P 71.41095 (publication No. 2,114,785). Solvents for said purpose are watermiscible solvents of the class of amides, alcohols, organic diol compounds and half-ethers thereof. Preferred watermiscible solvents are dimethylformamide, dimethylacetamide, N-methyl-2-pyrrolidinone, dimethyl sulfoxide, 1,3-dimethyl-2-imidazolidinone, and 3-methoxy-2-propanol. These solvents may be present in an amount in the range of 5 to 250 g per liter of the developer liquid. Further is mentioned polyvinylpyrrolidone acting as adsorbent for hydroquinone.

The developer formulation may be prepared in a concentrated form and diluted to a working strength just prior to use. Concentrated solutions for automatic processing are widely used in processing machines operating with a replenishment system.

Developer solutions used according to the present invention can be left in a machine processor for several weeks without marked degradation. The replenishment proceeds simply by adding a fresh amount of developer after discarding an exhausted portion.

The silver halide in the silver halide emulsions used according to the present invention may be any type of photosensitive silver halide.

The crystal form of the silver halide grains in the photographic emulsion may be regular (such as cubic or octahedral) or irregular (such as spherical or plate-like or a composite of these forms. The silver halide emulsion may comprise mixed grains of different size and crystal form. The interior and the surface layer of the silver halide grains may be different or the grains may be uniform throughout.

Two or more of separately prepared silver halide emulsions may be mixed and coated to form a single silver halide emulsion layer.

A preferred silver halide is of the type containing mainly silver chloride, e.g. contains at least 70 mole percent (more preferably at least 90 mole %) of silver chloride.

Another preferred type of silver halide is silver bromide-(iodide) the silver halide of which contains no more than 10 mole % of iodide, more preferably not more than 6 mole % of iodide.

The silver halide coverage may be equivalent with a coverage of silver in the range of 1.5 to 6 g/m$^2$, preferably in the range of 2 to 4 g of silver per m$^2$. The silver halide grain size is preferably in the range of 0.05 to 1 μm.

A silver halide emulsion material suitable for processing according to the present invention may be sensitized chemically according to any of the well-known techniques in emulsion making, e.g. by digesting with naturally active gelatin or various sulphur, selenium, tellurium compounds and/or gold compounds. The chemical sensitization may proceed not only with the sulfur compounds present inherently in photochemically active gelatin but likewise with thiosulfates, sulfites, thioureas, thiazoles or rhodanines. Reduction sensitization can be carried out with stannous salts, amines, formamidinesulfinic acid, silane compounds, e.g. methyldichlorosilane, hydrazine derivatives, aminoboranes, thiourea dioxide, etc. Specifically contemplated is the combined use of several of the preceding chemical ripening techniques, in particular, gold-sulfur combinations are highly preferred. The silver halide emulsion for use in the present invention may undergo likewise formation or physical ripening of the silver halide grains in the presence of a cadmium salt, a lead salt, a thallium salt, a rhodium salt or a complex salt thereof, an iridium salt or complex salt thereof or mixture of said salts and/or complexes.

A silver halide emulsion material suitable for processing according to the present invention may be sensitized spectrally, e.g. is ortho-sensitized or pan- and/or infrared-sensitized, with known spectral sensitizing dyes. For instance, the silver halide can be sensitized spectrally by treatment with a solution of a sensitizing dye in an organic solvent. Spectral sensitizers that may be used are e.g. the cyanines, merocyanines, complex (trinuclear) cyanines, complex (trinuclear) merocyanines, styryls, and hemicyanines. These sensitizing dyes may be used individually or as a combination thereof. A combination of sensitizing dyes is frequently used for super dye sensitization.

A silver halide emulsion material to be processed according to the present invention may also contain conventional addenda such as, plasticizers, surface active agents for assisting coating, antistatic agents, agents improving dispersibility, agents preventing sticking of the coated layer, fog-inhibiting compounds other than the already mentioned compound of general formula (Z), such as the mercapto derivatives of benzoxazole, benzthiazole, benzimidazole, benztriazole or tetrazole, particularly 1-phenyl-5-mercaptotetrazole and azaindene compounds, particularly 4-hydroxy substituted (1,3,3a,7)-tetraazaindenes.

Further the silver halide emulsion material may contain hardeners, e.g. aldehyde hardeners such as formaldehyde, mucochloric acid, glutardialdehyde and maleic dialdehyde, aziridines, oxypolysaccharides, dimethylurea, hydroxychlorotriazine, divinyl sulphones as described e.g. in U.S. Pat. No. 3,841,872, triacrylformal and/or N-carbamoylpyridinium sulfobetain compounds described in U.S.Pat. Nos. 3,880,665, 4,063,952 and published JP-A (Kokai) 89-119477/16.

The silver halide emulsions may contain any of the hydrophilic water-permeable binding materials known for that purpose. Suitable materials include gelatin, colloidal albumin, polyvinyl compounds, cellulose derivatives, acrylamide polymers etc. Mixtures of these binding agents may be used. The binding agents for the emulsion layer of the high contrast photographic element may also contain dispersed polymerized vinyl compounds. Such compounds are disclosed in e.g. the U.S. Pat. Nos. 3,142,568 of Robert William Nottorf, issued Jul. 28, 1964, 3,193,386 of Clayton F. A. White, issued Jul. 6, 1965, 3,062,674 of Robert Wong, issued Nov. 6, 1962, 3,220,844 of Robert C. Houck, Donald A. Smith and Joseph S. Yudelson, issued Nov. 30, 1965. They include the water-insoluble polymers of alkyl acrylates and methacrylates, acrylic acid, sulfoalkyl acrylates or methacrylates, copolymers of alkyl acrylates with acrylic acids, acryloyl-oxyalkyl sulphonic acids, acetoacetoxy alkyl acrylates such as 2-acetoacetoxyethyl methacrylate and the like. These compounds may be incorporated likewise into a layer separate from the silver halide emulsion layer of the photographic element. The vinyl polymers are generally employed in concentrations of about 20 to about 80%, most often in concentrations of at least 30% by weight based on the weight of the total binder content.

Silver halide emulsions wherein the binder partly consists of poly-N-vinylpyrrolidinone as described in U.S. Pat. No. 3,617,284 provide particularly high gradation results.

The silver halide emulsion layer(s) processed according to the present invention may be coated on a wide variety of supports. If desired, hydrophilic colloid layers are coated on one or both sides of the support.

Typical supports are cellulose nitrate film, cellulose ester film, polyvinyl acetal film, polystyrene film, poly(ethylene terephthalate) film, and related films or resinous materials, as well as glass, paper, metal and the like. Supports such as paper, which are coated with alpha-olefin polymers, particularly polymers of alpha-olefins containing two or more carbon atoms, as exemplified by polyethylene polypropylene, ethylene-butene copolymers and the like may be employed likewise.

In processing photographic elements according to the present invention, the time and temperature employed for development can be varied widely. Typically, the development temperature will be in the range of from about 20° C. to about 50° C., while the development time in rapid access normally lasts no longer than 90 s.

The following examples illustrate the invention without however limiting it thereto.

All ratios, percentages and amounts are by weight unless otherwise stated.

EXAMPLE 1

(comparative example)

A cubic grain type silver iodo-bromide (1 mole % of iodide) emulsion having an average grain size of 0.3 μm, chemically sensitized with ammonium gold(III) thiocyanate and sodium thiosulphate and stabilized with 4-hydroxy-6-methyl-(1,3,3a,7)-tetraazaindene was coated onto a subbed polyethylene terephthalate support at a gelatin coverage of 2.7 g per sq.m. and a coverage of silver halide equivalent with 3.2 g of silver per sq.m. The emulsion layer contained polyethyl acrylate latex and 5-nitro-indazole in amounts corresponding with 2 g/m$^2$ and 8 mg/m$^2$ respectively.

The silver halide emulsion layer was coated with a protective layer containing 0.6 g/m$^2$ of gelatin hardened with 1-(4-morfolinocarbamoyl)-4-(2-sulfoethyl)-pyridinium hydroxide inner salt. Separate area of the photographic material were exposed in a vertical process camera REPROMASTER RPS 2001 (trade name) through respectively a continuous tone wedge having a constant 0.15 and a grey negative screen for use in screen sensitometry having a screen ruling of 54 lines per cm.

The development proceeded by dipping the exposed photographic material into a tray for 45 s at a temperature of 30° C. (i.e. rapid access procedure) using a developer having the following composition:

| | |
|---|---|
| ethylenediamine tetra-acetic acid sodium salt | 1 g |
| sodium carbonate | 40 g |
| sodium bromide | 4 g |
| sodium sulphite | 70 g |
| hydroquinone | 40 g |
| N-methyl-2-pyrrolidinone | 30 ml |
| polyoxyethylene glycol | 200 mg |
| (average number of oxyethylene units being 70) | |
| water up to | 1 l |
| pH adjusted to 11.5 with sodium hydroxide. | |

To said composition 100 mg/liter of an antifogging compound (AFC) used according to the present invention and identified by number in Table 1 given hereinbefore is added as indicated in Table 2 furtheron, wherein test 6 relates to the use of 5-nitro-indazole as prior art anti-fogging agent No. X. The freshly prepared developer compositions are used in the development giving the sensitometric results presented in said Table 2.

The fixing proceeded for 3 min at 25° C. in a tray using a fixing bath having the following composition:

| | |
|---|---|
| ammonium thiosulphate (anhydrous) | 100 g |
| sodium sulphite (anhydrous) | 10 g |
| boric acid | 5 g |
| sodium acetate | 15 g |
| acetic acid, glacial | 8 ml |
| water to make | 1 l |

In said Table 2 the photographic speed is expressed in relative sensitivity values (rel. S) measured at density 3.0 above fog. The speed obtained with the developer containing 100 mg/l of compound No. 1 of Table 1 is arbitrarily given the value 100.

Gradient values in the toe ($\gamma_t$) of the sensitometric curve were measured between the log exposure values at densities 0.1 and 0.6 above fog on the log exposure scale of the sensitometric curve. Straight-line gradient (maximum gradient) values ($\gamma$), were measured between the log exposure values at densities 0.3 and 3.0 above fog on the log exposure scale of the sensitometric curve.

The screen dot quality was assessed and the rating expressed by numbers, wherein increasing numbers stand for degrading quality.

Number 0 stands for developed screen dots having high optical density and sharp, non-indented edges. The other numbers relate to screen dots having gradually reduced optical density and dot edges with increasing indentation and fuzzy structure. Larger than rating value 3 the quality is considered to be no longer commercially acceptable.

TABLE 2

| Test No. | AFC No. | rel. S | $\gamma_t$ | $\gamma$ | dot quality rating |
|---|---|---|---|---|---|
| 1 | 1 | 100 | 3.5 | 8.1 | 1-2 |
| 2 | 2 | 86 | 3.6 | 9.6 | 1 |
| 3 | 3 | 166 | 3.5 | 6.5 | 2 |
| 4 | 4 | 100 | 3.0 | 8.3 | 1-2 |
| 5 | 5 | 330 | 2.9 | 6.9 | 2-3 |
| 6 | X | 223 | 5.7 | 10.2 | 1 |

In order to check the stability of the above developer compositions of tests No. 1-6, these compositions were kept for 4 weeks at 60° C. in a closed plastic bottle. After said treatment the compositions were used again in the development of the photographic material as defined above and the sensitometric results were noticed and listed in Table 3 hereinafter. The relative speed value (rel. S), the gradient value in the toe ($\gamma_t$), the straight-line gradient (maximum gradient) value ($\gamma$) and dot quality were measured as defined above.

TABLE 3

| Test No. | AFC No. | rel. S | $\gamma_t$ | $\gamma$ | dot quality rating |
|---|---|---|---|---|---|
| 1' | 1 | 100 | 3.4 | 8.4 | 1-2 |
| 2' | 2 | 88 | 3.5 | 9.2 | 1 |
| 3' | 3 | 166 | 3.7 | 8.1 | 2 |
| 4' | 4 | 100 | 4.0 | 7.7 | 1-2 |
| 5' | 5 | 330 | 3.0 | 7.1 | 2-3 |
| 6' | X | 388 | 1.9 | 4.8 | 5 |

From these gradient and dot quality results can be learned that the antifogging compounds AFC 1-5 have a remarkable stabilizing effect, whereas the classical 5-nitro-indazole of test 6' fails in that respect.

EXAMPLE 2

A fine grain (average grain size: 0.3 μm) silver chloro-bromide emulsion comprising 16 mole % of bromide was coated onto a subbed polyethylene terephthalate support at a gelatin coverage of 3.6 g per sq.m. and a coverage of silver halide equivalent with 4.1 g of silver.

The silver halide was chemically sensitized with gold(III) chloride and sodium thiosulfate and spectrally sensitized to blue 400 to 500 nm) light. The silver halide emulsion layer was covered with a protective layer containing 0.9 g/m$^2$ of gelatin hardened with formaldehyde and containing 0.25 g/m$^2$ of hydroquinone.

The thus obtained photographic material was exposed and developed as defined above in Example 1 using compound No. 2.

The sensitometric results (rel. S, $\gamma_t$, $\gamma$ and dot quality were practically the same for the development with fresh and artificially aged (heat-treated) developer.

EXAMPLE 3

The photographic material of Example 1 was exposed and developed as defined in said Example 1 with the proviso that only compound No. 2 was used as anti-fogging agent and for comparative test purposes 0.50 mmole/liter of an auxiliary developing agent (AD1, AD2, AD3 or AD4) as identified in the following Table 4 was added to the developer composition of Example 1. The use of an auxiliary developing agent is in favour of a shorter developing time and rapid access to the image.

The relative speed value (rel. S), the gradient value in the toe ($\gamma_t$), the straight-line gradient (maximum gradient) value ($\gamma$) and dot quality were measured as defined above and are mentioned in relationship with the applied auxiliary developing agent in Table 4.

AD1 is p-amino-phenol
AD2 is 1-p-carboxyphenyl-4,4 dimethyl-3-pyrazolidinone
AD3 is p-phenylene diamine sulphate
AD4 is N,N-diethyl-p-phenylene diamine hydrochloride.

TABLE 4

| Test No. | auxiliary developing agent | rel. S | $\gamma_t$ | $\gamma$ | dot quality rating |
|---|---|---|---|---|---|
| 7 | AD1 | 103 | 2.9 | 6.9 | 2-3 |
| 8 | AD2 | 92 | 3.5 | 7.9 | 1-2 |
| 9 | AD3 | 94 | 3.6 | 8.5 | 1-2 |
| 10 | AD4 | 110 | 2.9 | 7.2 | 2-3 |

From these results can be learned that the identified auxiliary developing agents in the defined minor amount with respect to the principal developing agent (hydroquinone) and anti-fogging agent are useful for graphic art quality development.

We claim:

1. A developer liquid adapted for the photographic development of photographic silver halide emulsion layer materials and which comprises:
   1) A photographic developing agent consisting essentially of a hydroquinone;
   2) An inorganic compound yielding sulfite ions in an amount of at least 9 grams per liter of developing liquid;
   3) At least one organic anti-fogging agent corresponding to the following general formula (Z):

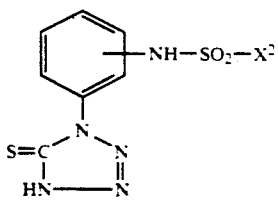

wherein:

X² represents an alkyl group, an aryl group, or an amino group, the amount of said anti-fogging agent being in the range of 50 mg to 1 g per liter of liquid;
4) A polyoxyalkylene polymer; and
5) An alkaline material in an amount imparting to the developer liquid a Ph of at least 10.5.

2. A developer liquid according to claim 1, wherein the sulphite ions are derived from an alkaline metal hydrogen bisulphite or metabisulphite or a corresponding ammonium salt.

3. A developer liquid according to claim 1, wherein said liquid contains free sulphite ions in a concentration in the range of 15 to 80 grams per liter.

4. A developer liquid according to claim 1, wherein in said anti-fogging agent X² is methyl, cetyl, phenyl, p-tolyl or p-nitro-phenyl.

5. A developer liquid according to claim 1, wherein said polyoxyalkylene polymer is present in a concentration up to 2500 mg per liter.

6. A developer liquid according to claim 1, wherein said liquid contains free bromide ions in the range of 0.5 to 15.0 g per liter of developer liquid.

7. A developer liquid according to claim 1, wherein said liquid contains at least one organic solvent for improving the dissolution of said hydroquinone in aqueous medium.

8. A developer liquid according to claim 7, wherein said organic solvent is a watermiscible organic solvent selected from the group consisting of dimethylformamide, dimethylacetamide, N-methyl-2-pyrrolidinone, dimethyl sulfoxide, 1,3-dimethyl-2-imidazolidinone, and 3-methoxy-2-propanol.

9. A developer liquid according to claim 7, wherein such organic solvent is present in an amount in the range of 5 to 250 g per liter of the developer liquid.

10. The liquid developer according to claim 1 wherein said photographic developing agent includes in addition to said hydroquinone at least one auxiliary developing agent in an amount less than about 10 mole percent of said hydroquinone.

11. A developer liquid according to claim 10, wherein the auxiliary developing agent is p-amino-phenol, p-methylaminophenol, p-phenylene diamine sulphate, N,N-diethyl-p-phenylene diamine hydrochloride or a 1-phenyl-3-pyrazolidinone type developing agent or a mixture of at least two of them.

12. A developer liquid according to claim 11, wherein said auxiliary developing agent is 1-p-carboxyphenyl-4,4-dimethyl-3-pyrazolidinone.

13. A method for high contrast development of image-wise exposed photographic silver halide layer material which comprises the step of contacting the exposed photographic material with an aqueous alkaline developing liquid having a Ph of at least 10.5 in the presence of the following ingredients:

1) A photographic developing agent consisting essentially of a hydroquinone;
2) An inorganic compound yielding sulfite ions in an amount of at least 9 grams per liter of developing liquid;
3) At least one organic anti-fogging agent corresponding to the following general formula (Z):

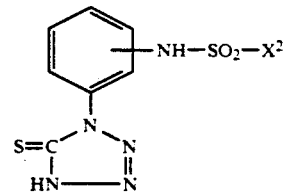

wherein:

X² represents an alkyl group, an aryl group, or an amino group; and
4) A polyoxyalkylene polymer having a molecular weight of at least 1500;

said ingredients 1), 2), 3) and 4) being present in effective amounts such that when the photographic material is exposed through a continuous tone wedge and contacted with said developing liquid for a time of 45 sec and photographically fixed, there is produced in said material a silver wedge image corresponding with a log exposure versus density sensitometric curve wherein the maximum gradient ($\gamma$) is at least 5 and the arithmetic product of said maximum gradient ($\gamma$) and of the gradient in the toe ($\gamma_t$) is at least 20; the maximum gradient is measured between the log exposure values corresponding with the densities 0.3 and 3.0 above fog for said curve; and the gradient for said toe is measured between the log exposure values corresponding with the densities 0.1 and 0.6 above fog of said curve.

14. The method according to claim 13 wherein said photographic developing agent includes in addition to said hydroquinone at least one auxiliary developing agent in an amount less than about 10 mole percent of said hydroquinone.

15. A method according to claim 14, wherein the developing agent is present in the photographic material already before development and incorporated therein already in the manufacturing stage, and the method comprises the step of contacting said photographic material with an alkaline aqueous liquid free from such developing agent but containing said ingredient 2) and optionally said other ingredients 3) and/or 4).

16. A method according to claim 13, wherein the coverage of such developing agent in said photographic material is in the range of 0.1 to 5 g/m².

17. A method according to claim 13, wherein at least one of said anti-fogging agents according to said general formula (Z) is added to the light-sensitive material already in its manufacturing stage.

18. A method according to claim 15, wherein at least one of said anti-fogging agents is added to the photographic material at a coverage up to 100 mg per m².

19. A method according to claim 14, wherein the auxiliary developing agent is p-amino-phenol, p-methylaminophenol, p-phenylene diamine sulphate, N,N-diethyl-p-phenylene diamine hydrochloride or a 1-phenyl-3-pyrazolidinone type developing agent or a mixture of at least two of them.

* * * * *